(12) United States Patent
Drake et al.

(10) Patent No.: US 11,844,893 B2
(45) Date of Patent: Dec. 19, 2023

(54) SHUNTS WITH BLOOD-FLOW INDICATORS

(71) Applicant: INSPIREMD LTD., Tel Aviv (IL)

(72) Inventors: Jesse Drake, Westborough, MA (US); Justin McCarthy, Northborough, MA (US); Itshak Cohen, Ramat Hasharon (IL)

(73) Assignee: INSPIRE M.D LTD., Tel Aviv (IL)

( * ) Notice: Subject to any disclaimer, the term of this patent is extended or adjusted under 35 U.S.C. 154(b) by 126 days.

(21) Appl. No.: 17/576,953

(22) Filed: Jan. 16, 2022

(65) Prior Publication Data

US 2022/0226556 A1    Jul. 21, 2022

Related U.S. Application Data

(60) Provisional application No. 63/138,451, filed on Jan. 17, 2021.

(51) Int. Cl.
  *A61M 1/36*     (2006.01)

(52) U.S. Cl.
  CPC ........ *A61M 1/3655* (2013.01); *A61M 1/3663* (2013.01); *A61M 1/3673* (2014.02)

(58) Field of Classification Search
  None
  See application file for complete search history.

(56) References Cited

U.S. PATENT DOCUMENTS

| | | |
|---|---|---|
| 3,641,994 A | 2/1972 | Gosling et al. |
| 4,559,034 A | 12/1985 | Kirita et al. |
| 4,661,097 A | 4/1987 | Fischell et al. |
| 4,874,359 A | 10/1989 | White et al. |
| 5,374,239 A * | 12/1994 | Mischenko ............. G01F 1/065 604/8 |
| 5,395,105 A | 3/1995 | Thommen, Jr. |
| 5,601,572 A * | 2/1997 | Middleman .......... A61B 18/082 606/139 |
| 5,843,244 A | 12/1998 | Pelton et al. |
| 6,019,772 A | 2/2000 | Shefaram et al. |

(Continued)

FOREIGN PATENT DOCUMENTS

| | | |
|---|---|---|
| CN | 100534392 C | 9/2009 |
| EP | 2497520 A1 | 9/2012 |
| WO | 2005051206 A1 | 6/2005 |
| WO | 2009012473 A2 | 1/2009 |
| WO | 2009100210 A1 | 8/2009 |
| WO | 2010075445 A1 | 7/2010 |
| WO | 2013022796 A2 | 2/2013 |
| WO | 2015100178 A1 | 7/2015 |

(Continued)

OTHER PUBLICATIONS

Sherif, "Homemade TCAR with Flow Reversal for Primary Proximal Carotid Artery Aneurisms in a Patent with Crescendo TIAS post neck operation," Linkedin post, pp. 1-2, year 2021, as downloaded from https://www.linkedin.com/posts/profsherifsultan_nuig-tcar-cast-activity-6710036851517902848-Qwzw.

(Continued)

*Primary Examiner* — Jonathan M Peo
(74) *Attorney, Agent, or Firm* — KLIGLER & ASSOCIATES PATENT ATTORNEYS LTD (57) ABSTRACT

An apparatus for shunting blood includes a flow-indication chamber shaped to define an entry port and an exit port, and one or more moveable objects disposed within the flow-indication chamber and configured to move in response to a flowing of the blood from the entry port to the exit port. At least a portion of a wall of the flow-indication chamber is transparent so as to expose the moveable objects to sight. Other embodiments are also described.

14 Claims, 4 Drawing Sheets

(56) References Cited

U.S. PATENT DOCUMENTS

| | | |
|---|---|---|
| 6,019,778 A | 2/2000 | Wilson et al. |
| 6,109,406 A | 8/2000 | Takagi et al. |
| 6,129,755 A | 10/2000 | Mathis et al. |
| 6,206,868 B1 | 3/2001 | Parodi |
| 6,235,042 B1 | 5/2001 | Katzman |
| 6,295,989 B1 | 10/2001 | Connors, III |
| 6,312,454 B1 | 11/2001 | Stoeckel et al. |
| 6,312,455 B2 | 11/2001 | Duerig et al. |
| 6,413,235 B1 | 7/2002 | Parodi |
| 6,423,032 B2 | 7/2002 | Parodi |
| 6,425,898 B1 | 7/2002 | Wilson et al. |
| 6,503,271 B2 | 1/2003 | Duerig et al. |
| 6,540,712 B1 | 4/2003 | Parodi et al. |
| 6,582,396 B1 | 6/2003 | Parodi |
| 6,632,236 B2 | 10/2003 | Hogendijk |
| 6,641,573 B1 | 11/2003 | Parodi |
| 6,645,222 B1 | 11/2003 | Parodi et al. |
| 6,682,505 B2 | 1/2004 | Bates et al. |
| 6,689,084 B2 | 2/2004 | Kaganov et al. |
| 6,743,219 B1 | 6/2004 | Dwyer et al. |
| 6,773,446 B1 | 8/2004 | Dwyer et al. |
| 6,859,986 B2 | 3/2005 | Jackson et al. |
| 6,863,685 B2 | 3/2005 | Davila et al. |
| 6,905,490 B2 | 6/2005 | Parodi |
| 6,908,474 B2 | 6/2005 | Hogendijk et al. |
| 6,935,404 B2 | 8/2005 | Duerig et al. |
| 6,936,060 B2 | 8/2005 | Hogendijk et al. |
| 6,942,688 B2 | 9/2005 | Bartholf et al. |
| 7,063,685 B2 | 6/2006 | Rome |
| 7,344,527 B2 | 3/2008 | Schweikert et al. |
| 7,879,011 B2 | 2/2011 | Chang |
| 7,927,347 B2 | 4/2011 | Hogendijk et al. |
| 7,998,104 B2 | 8/2011 | Chang |
| 8,002,728 B2 | 8/2011 | Chang |
| 8,157,760 B2 | 4/2012 | Criado et al. |
| 8,235,943 B2 | 8/2012 | Breznock et al. |
| 8,308,709 B2 | 11/2012 | Chang |
| 8,343,089 B2 | 1/2013 | Chang |
| 8,414,516 B2 | 4/2013 | Chang |
| 8,444,586 B2 | 5/2013 | Beck |
| 8,545,432 B2 | 10/2013 | Renati et al. |
| 8,545,552 B2 | 10/2013 | Garrison et al. |
| 8,574,245 B2 | 11/2013 | Garrison et al. |
| 8,740,834 B2 | 6/2014 | Criado et al. |
| 8,784,355 B2 | 7/2014 | Criado et al. |
| 8,858,490 B2 | 10/2014 | Chou et al. |
| 8,870,805 B2 | 10/2014 | Chang |
| 9,011,364 B2 | 4/2015 | Criado et al. |
| 9,011,467 B2 | 4/2015 | Garrison et al. |
| 9,084,857 B2 | 7/2015 | Cully et al. |
| 9,126,018 B1 | 9/2015 | Garrison |
| 9,138,527 B2 | 9/2015 | Renati et al. |
| 9,179,909 B2 | 11/2015 | Garrison et al. |
| 9,241,699 B1 | 1/2016 | Kume et al. |
| 9,259,215 B2 | 2/2016 | Chou et al. |
| 9,265,512 B2 | 2/2016 | Garrison et al. |
| 9,295,817 B2 | 3/2016 | Chang |
| 9,399,118 B2 | 7/2016 | Kume et al. |
| 9,427,305 B2 | 8/2016 | Kuraguntla et al. |
| 9,492,637 B2 | 11/2016 | Garrison et al. |
| 9,526,504 B2 | 12/2016 | Chang |
| 9,561,345 B2 | 2/2017 | Garrison et al. |
| 9,623,228 B2 | 4/2017 | Ryan et al. |
| 9,655,755 B2 | 5/2017 | Chou et al. |
| 9,662,118 B2 | 5/2017 | Chang |
| 9,662,480 B2 | 5/2017 | Kume et al. |
| 9,668,743 B2 | 6/2017 | Cully et al. |
| 9,669,183 B2 | 6/2017 | Chang |
| 9,669,191 B2 | 6/2017 | Chou et al. |
| 9,693,789 B2 | 7/2017 | Garrison et al. |
| 9,789,242 B2 | 10/2017 | Criado et al. |
| 9,820,761 B2 | 11/2017 | Garrison et al. |
| 9,833,555 B2 | 12/2017 | Criado et al. |
| 9,861,783 B2 | 1/2018 | Garrison et al. |
| 10,039,906 B2 | 8/2018 | Kume et al. |
| 10,085,864 B2 | 10/2018 | Chou et al. |
| 10,159,479 B2 | 12/2018 | Hentges et al. |
| 10,182,801 B2 | 1/2019 | Garrison |
| 10,188,399 B2 | 1/2019 | Chang |
| 10,226,563 B2 | 3/2019 | Garrison et al. |
| 10,226,598 B2 | 3/2019 | Chou et al. |
| 10,238,853 B2 | 3/2019 | Kume et al. |
| 10,272,269 B2 | 4/2019 | Garrison et al. |
| 10,286,139 B2 | 5/2019 | Criado et al. |
| 10,327,790 B2 | 6/2019 | Garrison et al. |
| 10,328,232 B2 | 6/2019 | Chang |
| 10,357,242 B2 | 7/2019 | Garrison et al. |
| 10,369,346 B2 | 8/2019 | Ryan et al. |
| 10,384,034 B2 | 8/2019 | Garrison et al. |
| 10,390,847 B2 | 8/2019 | Garrison et al. |
| 10,426,497 B2 | 10/2019 | Chou et al. |
| 10,426,885 B2 | 10/2019 | Criado et al. |
| 10,485,917 B2 | 11/2019 | Criado et al. |
| 10,543,307 B2 | 1/2020 | Criado et al. |
| 10,709,832 B2 | 7/2020 | Criado et al. |
| 10,722,239 B2 | 7/2020 | Chang |
| 10,779,835 B2 | 9/2020 | Chang |
| 10,779,855 B2 | 9/2020 | Garrison |
| 10,799,244 B2 | 10/2020 | Cully et al. |
| 10,799,669 B2 | 10/2020 | Chou et al. |
| 10,828,460 B2 | 11/2020 | Chang |
| 10,864,357 B2 | 12/2020 | Kume et al. |
| 10,881,393 B2 | 1/2021 | Hentges et al. |
| 10,918,504 B2 | 2/2021 | Wallace et al. |
| 10,925,709 B2 | 2/2021 | Rogers et al. |
| 10,939,929 B2 | 3/2021 | Garrison et al. |
| 10,952,882 B2 | 3/2021 | Chou et al. |
| 10,973,502 B2 | 4/2021 | Garrison |
| 11,020,133 B2 | 6/2021 | Wilson et al. |
| 11,027,104 B2 | 6/2021 | Kume et al. |
| 11,097,132 B2 | 8/2021 | Garrison et al. |
| 11,103,627 B2 | 8/2021 | Garrison et al. |
| 11,141,259 B2 | 10/2021 | MacDonald et al. |
| 2001/0047184 A1 | 11/2001 | Connors, III |
| 2002/0087119 A1 | 7/2002 | Parodi |
| 2007/0055296 A1* | 3/2007 | Stergiopulos ......... A61B 17/12 606/158 |
| 2010/0204684 A1 | 8/2010 | Garrison et al. |
| 2011/0004147 A1 | 1/2011 | Renati et al. |
| 2013/0041305 A1 | 2/2013 | Tarlian, Jr. et al. |
| 2013/0317409 A1 | 11/2013 | Cully et al. |
| 2014/0296769 A1 | 10/2014 | Hyde et al. |
| 2016/0242764 A1 | 8/2016 | Garrison et al. |
| 2019/0344058 A1 | 11/2019 | Hakim |
| 2019/0351182 A1 | 11/2019 | Chou et al. |
| 2019/0358443 A1 | 11/2019 | Lopez et al. |
| 2020/0292367 A1 | 9/2020 | Elizalde |
| 2020/0397472 A1 | 12/2020 | MacDonald et al. |
| 2021/0145453 A1 | 5/2021 | Kume |
| 2021/0298929 A1 | 9/2021 | Wallace et al. |

FOREIGN PATENT DOCUMENTS

| | | |
|---|---|---|
| WO | 2016018781 A1 | 2/2016 |
| WO | 2016036660 A1 | 3/2016 |
| WO | 2016164606 A1 | 10/2016 |
| WO | 2016176409 A1 | 11/2016 |
| WO | 2018017981 A1 | 1/2018 |
| WO | 2018156574 A1 | 8/2018 |
| WO | 2019010077 A1 | 1/2019 |
| WO | 2021087363 A1 | 5/2021 |
| WO | 2021087480 A1 | 5/2021 |
| WO | 2022201081 A1 | 9/2022 |

OTHER PUBLICATIONS

Silk Road Medical, Inc., "Enroute Transcarotid Neuroprotection System", Manual, pp. 1-20, Mar. 7, 2020, year 2022, as downloaded from file:///C:/Users/Miriam/Downloads/_https___silkroadmed.com_wp-content_uploads_2020_09_11858.7-ENROUTE-NPS-IFU-US-ARTWORK1%20(1).pdf.

(56) References Cited

OTHER PUBLICATIONS

Parodi et al., "Cerebral Protection During Carotid Stenting Using Flow Reversal," Journal of Vascular Surgery, vol. 41, No. 3, pp. 416-422, year 2005.

Perez-Grueso et al., "Angioplastia y Stenting Carotideo por Miniacceso Cervical y Flujo Invertido," Angiologia, vol. 56, supl. 1, pp. S225-S234, year 2004.

Luk et al., "Transcarotid Artery Revascularization as a New Modality of Treatment for Carotid Stenosis," Journal Pre-proof, Annals of Vascular Surgery, Elsevier Inc., pp. 1-14, year 2019.

Chang et al., "A New Approach to Carotid Angioplasty and Stenting with Transcervical Occlusion and Protective Shunting: Why it May be a Better Carotid Artery Intervention," Journal of Vascular Surgery, vol. 39, No. 5, pp. 994-1002, May 2004.

Lin et al., "Protected Carotid Artery Stenting and Angioplasty via Transfemoral versus Transcervical Approaches," Vascular and Endovascular Surgery, vol. 39, No. 6, pp. 499-503, year 2005.

Silk Road Medical, "TransCarotid Artery Revascularization (TCAR)," Product Overview, pp. 1-6, year 2022, as downloaded from https://silkroadmed.com/patient-caregivers/the-tcar-procedure/.

Rhodes et al., "Arteriovenous Shunt Measurements in Extremities," Journal of Nuclear Medicine, vol. 13, No. 6, pp. 357-362, year 1972.

"Qosina—Medical Device Components/OEM Components," product catalogue, Qosina Corp., USA, Qosina Europe Srl., Italy, pp. 1-4, year 2022, as downloaded from https://www.qosina.com/.

International Application PCT/IB2022/052688 filed Mar. 24, 2022.

Drake et al., U.S. Appl. No. 63/211,025, filed Jun. 16, 2021.

Inspiremd, "Sustained Embolic Protection", pp. 1-23, Jul. 8, 2020, as downloaded from https://www.inspiremd.com/en/wp-content/uploads/InspireMD-Investor-Deck-Revised-July-8-2020_compressed.pdf.

Sherif, "The TCAR Procedure: Transcervical carotid Artery Revascularization and stenting by C-Guard", Linkedin post, p. 1-1, year 2021, as downloaded from https://www.linkedin.com/feed/update/urn:li:activity:6689646427859140608/.

International Application # PCT/IB2022/050329 Search Report dated May 10, 2022.

International Application # PCT/IBB2022/052688 Search Report dated Jul. 7, 2022.

Saint-Gobain Performance Plastics Corporation, "TYGON Medical/Surgical Tubing S-50-HL," pp. 1-2, year 2004.

Silk Road Medical Inc., "ENHANCE Transcarotid Peripheral Access Kit," pp. 1-2, Dec. 28, 2018.

Silk Road Medical Inc., "ENROUTE Transcarotid Stent System," pp. 1-4, May 27, 2021.

\* cited by examiner

SHUNTS WITH BLOOD-FLOW INDICATORS

CROSS-REFERENCE TO RELATED APPLICATIONS

The present application claims the benefit of U.S. Provisional Application 63/138,451, entitled "Visualization of blood flow in a venous/arterial shunting system," filed Jan. 17, 2021, whose disclosure is incorporated herein by reference.

FIELD OF THE INVENTION

The present invention relates to medical procedures, such as procedures in which blood of a subject is shunted from one blood vessel to another.

BACKGROUND

In some procedures, blood is shunted from one blood vessel to another.

SUMMARY OF THE INVENTION

There is provided, in accordance with some embodiments of the present invention, an apparatus for shunting blood. The apparatus includes a flow-indication chamber shaped to define an entry port and an exit port, and one or more moveable objects disposed within the flow-indication chamber and configured to move in response to a flowing of the blood from the entry port to the exit port. At least a portion of a wall of the flow-indication chamber is transparent so as to expose the moveable objects to sight.

In some embodiments, the moveable objects include a plurality of beads.

In some embodiments, at least one of the beads includes multiple faces.

In some embodiments, each of the beads is coated with an anticoagulant.

In some embodiments, the moveable objects include a rotational member configured to rotate in response to the blood exerting a force on the rotational member.

In some embodiments, the rotational member includes a wheel including a plurality of spokes.

In some embodiments, the wheel is positioned relative to the entry port and exit port such that each of the spokes, when perpendicular to an unimpeded path of the blood from the entry port to the exit port, intersects the unimpeded path.

In some embodiments, a most proximal point on each of the spokes that intersects the unimpeded path is located between 50% and 80% of a length of the spoke from a proximal end of the spoke.

In some embodiments, the apparatus further includes a filter chamber configured to couple to the flow-indication chamber and to hold a blood filter in the filter chamber.

In some embodiments, the apparatus further includes a threaded ring, the filter chamber is shaped to define a filter-chamber port, the flow-indication chamber is configured to screw into a first side of the threaded ring, and the filter chamber is configured to screw into a second side of the threaded ring such that the entry port or exit port is fluidly connected with the filter-chamber port.

In some embodiments, the flow-indication chamber is further configured to hold a blood filter therein.

In some embodiments, the apparatus further includes a valve configured to regulate the flowing of the blood through a port selected from the group of ports consisting of: the entry port, and the exit port.

In some embodiments, the valve includes:

a pushable element passing through a wall of the flow-indication chamber and configured to cover the port upon being pushed into the flow-indication chamber; and a spring coupled to the pushable element and to an inner wall of the flow-indication chamber, and configured to inhibit the pushable element from covering the port in an absence of any pushing force applied to the pushable element.

In some embodiments, the spring includes a tension spring.

There is further provided, in accordance with some embodiments of the present invention, a method including coupling an upstream end of a first conduit to a source blood vessel of a subject and a downstream end of the first conduit to an entry port of a shunt. The method further includes coupling an upstream end of a second conduit to an exit port of the shunt and a downstream end of the second conduit to a sink blood vessel of the subject, such that blood flows from the source blood vessel to the sink blood vessel via the shunt, thus causing movement of one or more moveable objects disposed within the shunt, the movement being visible through a wall of the shunt.

In some embodiments, the shunt includes a flow-indication chamber, which contains the moveable objects, and a filter chamber, which is coupled to the flow-indication chamber and holds a blood filter in the filter chamber.

There is further provided, in accordance with some embodiments of the present invention, an apparatus including a chamber shaped to define a fluid port, a first appendage protruding from the chamber and shaped to define a first aperture and a first row of one or more teeth, and a second appendage protruding from the chamber and shaped to define a second aperture and a second row of one or more teeth parallel to the first row of teeth. The second row is configured to interlock with the first row at multiple different relative positions of the first appendage and second appendage in which the second aperture is aligned with the first aperture with different respective degrees of alignment such that a tube, which carries blood to or from the fluid port through the first aperture and second aperture, is constricted with different respective degrees of constriction.

In some embodiments, the chamber is configured to hold a blood filter therein.

In some embodiments, the apparatus further includes one or more moveable objects disposed within the chamber and configured to move in response to a flowing of the blood through the chamber, at least a portion of a wall of the chamber being transparent so as to expose the moveable objects to sight.

In some embodiments, the first appendage and second appendage are continuous with a wall of the chamber.

In some embodiments, the first appendage and second appendage are configured to revert to a default relative position, in which the tube is not constricted, upon a release of the first row and second row from one another.

In some embodiments, the first appendage includes a first back arm, which protrudes from the chamber, and a first front arm, which is angled with respect to the first back arm and is shaped to define the first aperture and the first row of teeth, and the second appendage includes a second back arm, which protrudes from the chamber, and a second front arm, which is angled with respect to the second back arm and is shaped to define the second aperture and the second row of teeth.

In some embodiments, each of the teeth in the first row and in the second row is angled backward, such that an advancement of the first row and second row relative to one another constricts the tube.

In some embodiments, the tube is not completely constricted in any of the positions.

There is further provided, in accordance with some embodiments of the present invention, a method including sliding a first appendage, which protrudes from a chamber and is shaped to define a first aperture and a first row of one or more teeth, across a second appendage, which protrudes from the chamber and is shaped to define a second aperture and a second row of one or more teeth parallel to the first row of teeth, such that the second row interlocks with the first row at a relative position of the first appendage and second appendage in which the second aperture is misaligned with the first aperture, thereby constricting a tube that carries blood to or from a fluid port of the chamber through the first aperture and second aperture. The method further includes, subsequently to constricting the tube, releasing the first row and second row from one another, thereby causing the first appendage and second appendage to revert to a default relative position in which the tube is not constricted.

The present invention will be more fully understood from the following detailed description of embodiments thereof, taken together with the drawings, in which:

DETAILED DESCRIPTION OF EMBODIMENTS

Overview

In some cases, it may be necessary to shunt blood from one anatomical site to another. For example, during an operation to remove a clot from a carotid artery of a subject, it may be necessary to shunt blood from the carotid artery to a vein, such as a femoral vein, of the subject. In such cases, a shunting device (or "shunt") is used to carry blood between the sites. However, there is a risk of the blood flow through the shunt slowing or stopping without the physician noticing.

To mitigate this risk, embodiments of the present invention provide a shunt comprising a flow-indication chamber containing one or more moveable objects, which are configured to move in response to the flow of blood through the flow-indication chamber. At least a portion of the wall of the flow-indication chamber is transparent, such that the moveable objects are visible. For example, the wall may comprise a transparent window, and the moveable objects may be disposed behind the window. Thus, a physician may readily check whether the blood is flowing properly through the shunt, by observing the degree of motion of the moveable objects.

In some embodiments, the moveable objects comprise multiple beads suspended in the blood, which rotate and/or change position as the blood flows. In other embodiments, the moveable objects comprise a wheel comprising a plurality of radiating spokes, which rotates as the blood flows across the spokes.

Another challenge is that sometimes it may be necessary to slow or stop the flow of blood through the shunt temporarily, e.g., to allow more blood to flow through the carotid artery to the brain of the subject.

To address this challenge, some embodiments of the present invention equip the shunt with a valve configured to control the rate of flow through the entry port or exit port of the shunt. For example, the valve may comprise a pushable element passing through the wall of the aforementioned flow-indication chamber, along with a spring within the flow-indication chamber, which couples the pushable element to an inner wall of the flow-indication chamber. In its resting state, the spring holds the pushable element away from the port, such that blood freely flows through the port. On the other hand, a pushing force sufficient to overcome the force of the spring may push the pushable element over the port, thereby slowing or stopping the flow of blood.

In other embodiments, the shunt is equipped with a tube constrictor configured to constrict the tube carrying the blood to or from the port. The tube constrictor comprises a pair of parallel arms, which are shaped to define respective apertures and respective rows of teeth. The rows of teeth are configured to interlock with one another at a default position, in which the apertures are aligned with one another, and at one or more other positions, in which the apertures are misaligned by varying degrees. Thus, while the tube passes through the apertures, the tube may be partially or fully constricted by sliding the arms over one another. Subsequently to constricting the tube, to resume regular blood flow, the rows of teeth may be released from one another such that the arms revert to their default positions.

Apparatus Description

Figure 1:
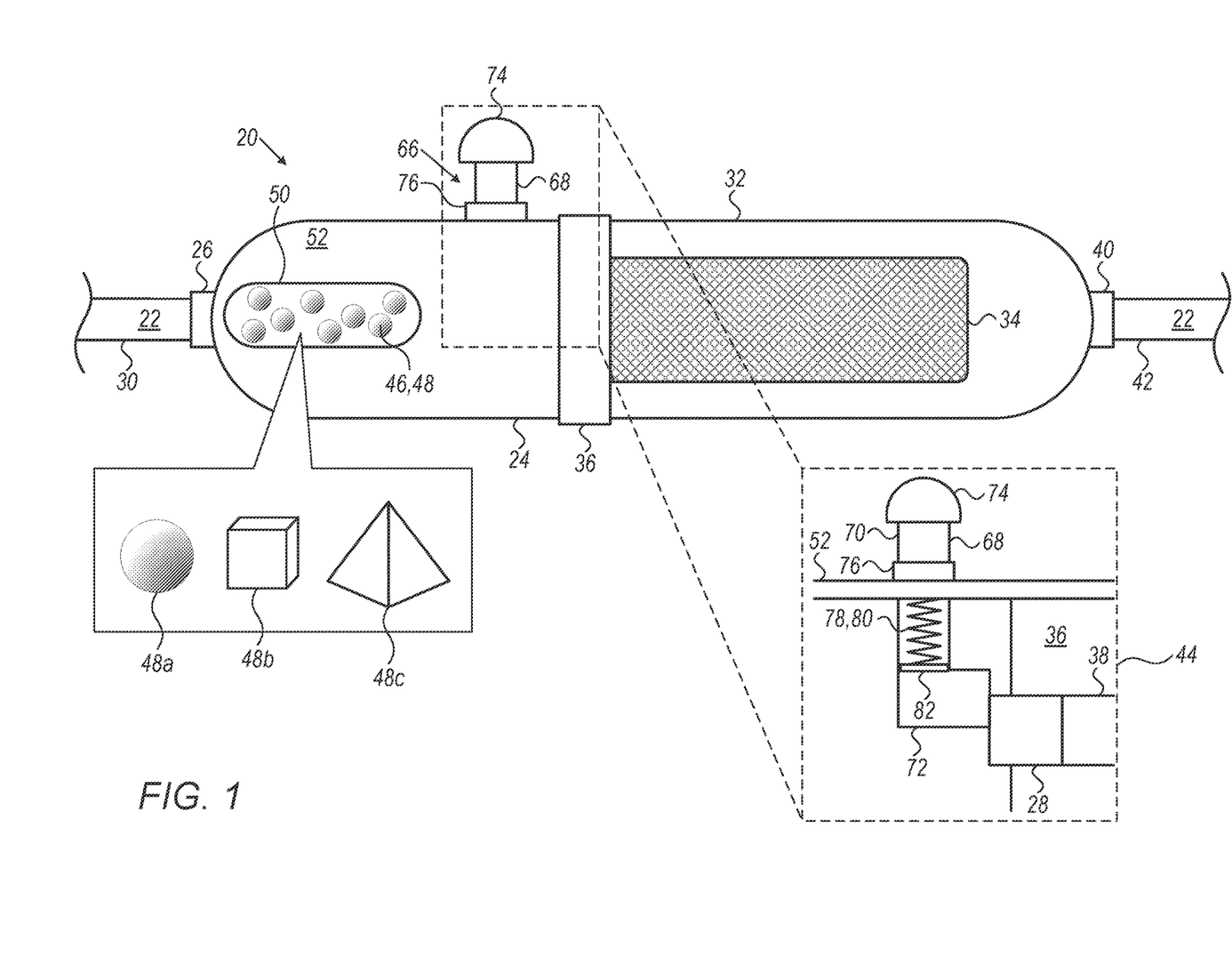
FIGS. 1-3 are schematic illustrations of an apparatus for shunting blood, in accordance with some embodiments of the present invention.

Reference is initially made to FIG. 1, which is a schematic illustration of an apparatus 20 for shunting blood 22, in accordance with some embodiments of the present invention. An inset portion 44 of FIG. 1 shows part of the interior of apparatus 20.

Apparatus 20, which may be referred to as a "shunt," comprises a flow-indication chamber 24 shaped to define an entry port 26 and an exit port 28. Blood 22 enters flow-indication chamber 24 via entry port 26, flows through the flow-indication chamber, and exits the flow-indication chamber via exit port 28.

In some embodiments, entry port 26 is configured to couple to an entry tube 30 (or any other entry conduit, such as a catheter) through which blood 22 flows to apparatus 20. For example, entry tube 30 may be fittingly inserted into entry port 26, or the entry port may be fittingly inserted into the entry tube.

Figure 3:
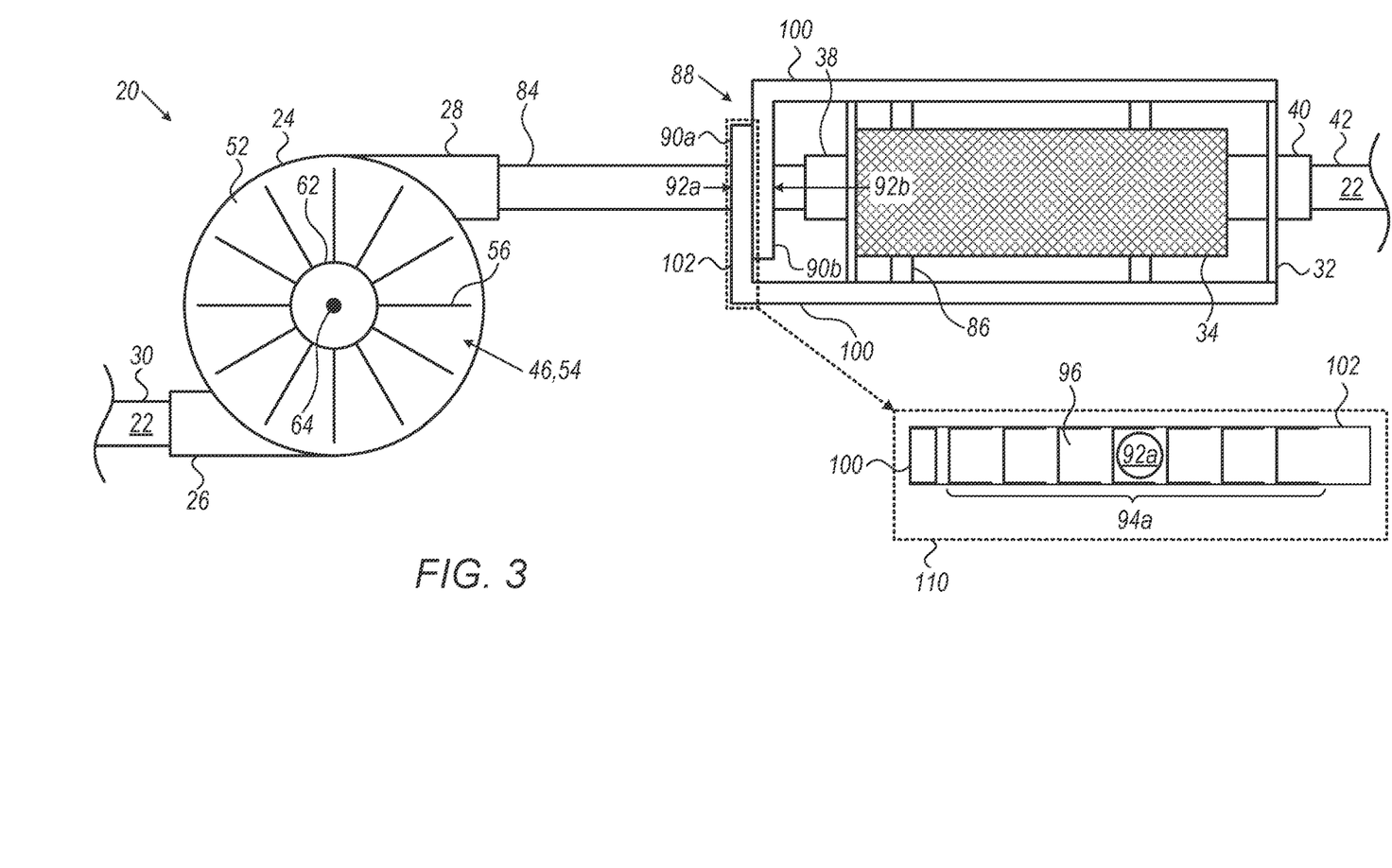

In some embodiments, apparatus 20 further comprises a filter chamber 32 configured to couple to flow-indication chamber 24 and to hold a blood filter 34 in filter chamber 32. Blood filter 34 may be secured within the filter chamber using any suitable structural components, such as a plurality of ribs 86 as shown in FIG. 3, which is described below. Filter chamber 32 is shaped to define an entry port 38, through which blood 22 enters the filter chamber, and an exit port 40, through which the blood exits the filter chamber.

As shown in FIG. 1, the filter chamber may be coupled to the flow-indication chamber downstream from the flow-indication chamber, such that the blood flows through the filter chamber after flowing through the flow-indication chamber. (Optionally, a single common port may function as both exit port 28 and entry port 38.) In such embodiments, exit port 40 is configured to couple to an exit tube 42 (or any other exit conduit, such as a catheter), which carries the blood from apparatus 20.

Alternatively, the filter chamber may be coupled to the flow-indication chamber upstream from the flow-indication chamber. (Optionally, a single common port may function as both exit port 40 and entry port 26.) In such embodiments, entry port 38 of the filter chamber is configured to couple to entry tube 30, and exit port 28 of the flow-indication chamber is configured to couple to exit tube 42.

In some embodiments, apparatus 20 further comprises a threaded ring 36. Flow-indication chamber 24 is configured to screw into one side of threaded ring 36, and filter chamber 32 is configured to screw into the other side of the threaded ring such that the two chambers are in fluid communication with one another. For example, as shown in FIG. 1, the flow-indication chamber may be screwed into the upstream side of ring 36 and the filter chamber may be screwed into the downstream side of ring 36, such that the blood flows directly from exit port 28 into entry port 38. Alternatively, the filter chamber may be screwed into the upstream side of ring 36 and the flow-indication chamber may be screwed into the downstream side of ring 36, such that the blood flows directly from exit port 40 into entry port 26.

In other embodiments, as shown in FIG. 3, the flow-indication chamber and filter chamber are coupled to one another via a coupling tube 84.

In yet other embodiments, apparatus 20 does not comprise filter chamber 32. In such embodiments, flow-indication chamber 24 may be configured to hold blood filter 34 therein.

Apparatus 20 may shunt blood 22 between any two suitable blood vessels of a human or animal subject. In other words, apparatus 20 may shunt blood 22 from any suitable "source" blood vessel of the subject to any suitable "sink" blood vessel of the subject. For example, apparatus 20 may shunt blood from an artery of the subject to a vein of the subject, with entry tube 30 delivering blood from the artery and exit tube 42 carrying the blood to the vein. As a specific example, apparatus 20 may shunt blood from a carotid artery to a femoral vein during an operation to remove a clot from the carotid artery. Alternatively, apparatus 20 may shunt blood from a higher-pressure artery to a lower-pressure artery.

To deploy apparatus 20, the upstream end of entry tube 30 is coupled to the source blood vessel (e.g., via a stopcock and/or any other suitable equipment), and the downstream end of the entry tube is coupled to the entry port of apparatus 20 (e.g., entry port 26, for embodiments in which the flow-indication chamber is upstream from the filter chamber). Similarly, the upstream end of exit tube 42 is coupled to the exit port of apparatus 20 (e.g., exit port 40, for embodiments in which the flow-indication chamber is upstream from the filter chamber), and the downstream end of the exit tube is coupled to the sink blood vessel (e.g., via a stopcock and/or any other suitable equipment). Subsequently, blood flows from the source blood vessel to the sink blood vessel via apparatus 20.

Blood-Flow Indicators

Apparatus 20 further comprises one or more moveable objects 46 disposed within flow-indication chamber 24 and configured to move in response to the flowing of blood 22 from entry port 26 to exit port 28. At least a portion of the wall 52 of the flow-indication chamber is transparent so as to expose moveable objects 46 to sight. For example, wall 52 may be entirely transparent, as shown in FIG. 3 (described below). Alternatively, as shown in FIG. 1, the wall may comprise at least one transparent window 50. Thus, the physician may readily check the rate of blood flow through the flow-indication chamber, by observing the degree of movement of moveable objects 46. In some embodiments, the transparent portion of wall 52 comprises a magnifying lens, configured to magnify moveable objects 46.

In some embodiments, moveable objects 46 comprise a plurality of beads 48, which rotate and/or change position as the blood flows. Typically, beads 48 have a density less than that of blood 22, such that the beads remain suspended in the blood. Beads 48 may comprise any suitable hemocompatible material such as a metal, plastic, wood, latex, synthetic rubber, or any combination of the above.

In general, each of the beads may have any suitable shape. For example, beads 48 may comprise at least one spherical bead 48a. Alternatively or additionally, beads 48 may comprise at least one bead comprising multiple faces; such a bead may move more in response to the blood flow, relative to spherical bead 48a, due to the greater force applied to the bead by the blood. Example of beads comprising multiple faces include a cubical bead 48b and a pyramidical bead 48c.

In general, larger beads may be more noticeable than smaller beads; hence, in some embodiments, for each bead 48, the Cartesian distance between any two points on the outer surface of the bead is greater than 0.1 cm. Alternatively or additionally, for increased movement of the bead, the Cartesian distance between any two points on the outer surface of the bead may be less than 0.65 cm.

In some embodiments, each of the beads is coated with an anticoagulant, such as heparin.

In some embodiments, for greater visibility, the color of the beads contrasts with that of blood 22. Suitable contrasting colors include black, blue, and white. Alternatively, the beads may have any other color.

In some embodiments, exit port 28 is covered with a filter configured to inhibit any of the beads from passing through. Alternatively or additionally, as described above, filter chamber 32 may be coupled to the flow-indication chamber downstream from the flow-indication chamber, such that any beads that pass through exit port 28 are filtered from the blood by filter 34.

Figure 2:
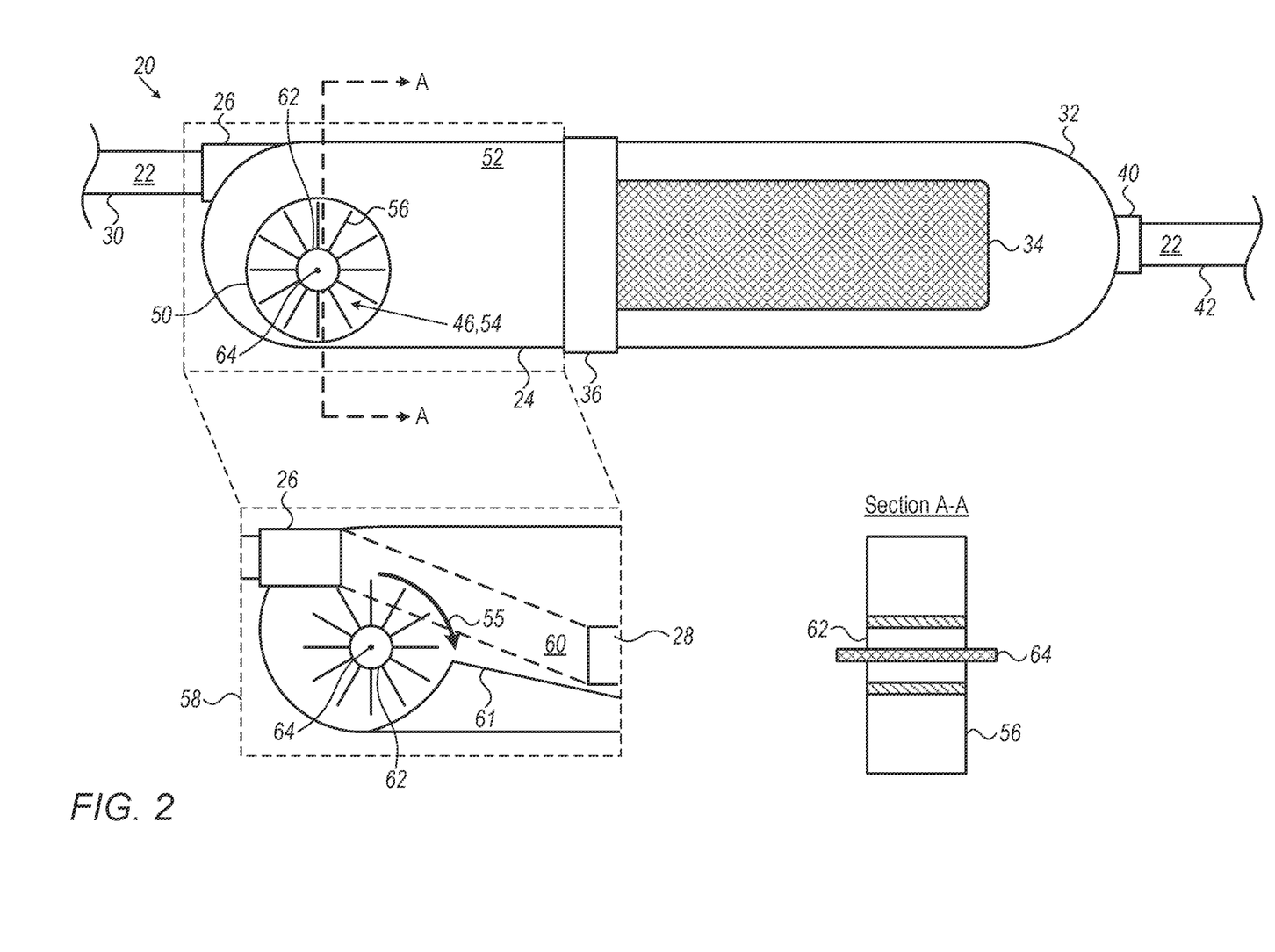

Reference is now made to FIG. 2, which is a schematic illustration of apparatus 20, in accordance with some embodiments of the present invention. An inset portion 58 of FIG. 2 shows part of the interior of apparatus 20.

In some embodiments, moveable objects 46 comprise a rotational member configured to rotate in response to the blood exerting a force on the rotational member.

For example, moveable objects 46 may comprise a wheel 54 comprising a plurality of spokes 56 (which may also be referred to as "radial members") and configured to rotate in response to blood 22 exerting a force on spokes 56. For noticeability, the length of each spoke 56 may be greater than 0.6 cm, and/or the width of each spoke may be greater than 0.3 cm. Alternatively or additionally, to obviate the need for an overly large flow-indication chamber, the length of each spoke 56 may be less than 3.8 cm, and/or the width of each spoke may be less than 1.3 cm.

Using two dashed lines, inset portion 58 demarcates the unimpeded path 60 of the blood, i.e., the path from entry port 26 to exit port 28 that the blood would follow in the absence of wheel 54. Typically, wheel 54 is positioned relative to the entry and exit ports such that each spoke, when perpendicular to path 60 at any point along the path, intersects the path. Thus, the flow of blood through the flow-indication chamber generally keeps the wheel rotating in a single direction. For example, in FIG. 2, the wheel rotates clockwise, as indicated by a rotation indicator 55.

For example, denoting the end of the spoke closest to hub 62 as the proximal end of the spoke and the opposite end as the distal end of the spoke, the most proximal point on the spoke that intersects path 60 may be located between 50% and 80% of the length of the spoke from the proximal end of the spoke. (For example, if the spoke is 3 cm long, the most proximal point on the spoke that intersects path 60 may be located between 1.5 and 2.4 cm from the proximal end of the spoke.) Advantageously, this positioning of the wheel may increase the rotational force to which the wheel is subjected.

In some embodiments, the internal walls 61 of flow-indication chamber 24 constrict the space within the chamber in which the blood can flow, such that the blood follows path 60 at a greater speed and hence, applies greater force to the rotational member.

Typically, as shown in Section A-A, wheel 54 is mounted onto a shaft 64 (i.e., shaft 64 passes through hub 62), such that the wheel rotates about the shaft. Shaft 64 is coupled at each of its ends to wall 52.

The rotational member (e.g., wheel 54) may be any suitable color, including a color that contrasts with that of blood, as described above for beads 48 (FIG. 1).

In alternative embodiments, Doppler ultrasound is used to measure the rate of blood flow. For example, a fixture, shaped to define a socket, may be fitted over one of the tubes, and a standard Doppler ultrasound probe may be inserted into the socket.

Regulating Blood Flow

Reference is again made to FIG. 1.

In some embodiments, apparatus 20 further comprises a valve 66 configured to regulate the flow of blood through the flow-indication chamber. Thus, using valve 66, a physician may control the rate at which blood is shunted.

In some embodiments, valve 66 comprises a pushable element 68 passing through wall 52 and configured to cover entry port 26 or exit port 28 upon being pushed into the flow-indication chamber. Typically, a gasket 76 (made of rubber, for example) seals the aperture in wall 52 through which the pushable element passes, such that blood does not leak through the wall.

In such embodiments, valve 66 further comprises a spring 78 coupled to the pushable element (e.g., by virtue of being coupled to a ledge 82 coupled to the pushable element) and to an inner wall of the flow-indication chamber (e.g., the inside of wall 52). Spring 78 is configured to inhibit the pushable element from covering the entry port or exit port in the absence of any pushing force applied to the pushable element. Thus, to slow or stop the flow of blood, the physician must continuously exert a pushing force to counteract the force applied by the spring, such that the physician is unlikely to forget that the flow has been slowed or stopped.

Typically, as shown in FIG. 1, spring 78 comprises a tension spring 80. In the absence of any pushing force, spring 80 is maximally compressed, such that the tension spring holds the pushable element in its outermost position.

In some embodiments, pushable element 68 comprises a neck 70 and a foot 72, which protrudes from the end of neck 70 that is inside the flow-indication chamber. As neck 70 is pushed further into the flow-indication chamber, foot 72 covers a greater portion of the entry port or exit port, thereby slowing the flow of blood. Upon the neck being maximally pushed, foot 72 completely covers the port, such that the flow is stopped. Optionally, the opposite end of neck 70, which is outside the flow-indication chamber, may terminate at a head 74, which is wider than the neck and thus facilitates the pushing of the neck into the flow-indication chamber.

In other embodiments, valve 66 comprises a pullable element passing through wall 52 and configured to cover entry port 26 or exit port 28 upon being pulled.

(It is noted that valve 66 may also be combined with any other suitable embodiment of moveable objects 46, such as the embodiment of FIG. 2.)

Reference is now made to FIG. 3, which is a schematic illustration of apparatus 20, in accordance with some embodiments of the present invention.

In some embodiments, apparatus 20 comprises tube constrictor 88, which may also be referred to as a "locking clip." Tube constrictor 88 comprises a first appendage 90*a*, shaped to define a first aperture 92*a*, and a second appendage 90*b*, shaped to define a second aperture 92*b*.

As further described below with reference to FIGS. 4A-B, tube constrictor 88 is configured to control the rate of blood flow through a tube passing through apertures 92*a* and 92*b* by constricting the tube with varying degrees of constriction. Thus, apparatus 20 need not necessarily comprise valve 66 (FIG. 1).

For example, tube constrictor 88 may provide two degrees of constriction: no (0%) constriction, and full (100%) or partial (e.g., 80%-90%) constriction. Alternatively, tube constrictor 88 may provide three or more degrees of constriction. An example of four degrees of constriction is 0%, 20%-40% (e.g., 33%), 60%-80% (e.g., 66%), and 90%-100%.

(In the context of the present application, including the claims, the tube may be considered to be constricted by x % if the rate of blood flow through the tube is x % of what the rate would be if the tube were not constricted at all.)

In some such embodiments, flow-indication chamber 24 is coupled to filter chamber 32 via coupling tube 84, and tube constrictor 88 is configured to constrict the coupling tube. For example, as shown in FIG. 3, first appendage 90*a* and second appendage 90*b* may protrude from filter chamber 32 in the upstream direction, i.e., the first and second appendages may protrude beyond entry port 38, and coupling tube 84 may carry blood to entry port 38 through the first and second apertures. Alternatively, the first and second appendages may protrude from flow-indication chamber 24 in the downstream direction, i.e., the first and second appendages may protrude beyond exit port 28, and coupling tube 84 may carry blood from exit port 28 through the first and second apertures.

In other such embodiments, tube constrictor 88 is configured to constrict entry tube 30. In other words, first appendage 90*a* and second appendage 90*b* protrude from flow-indication chamber 24 in the upstream direction, i.e., the first and second appendages protrude beyond entry port 26, and entry tube 30 carries blood to entry port 26 through the first and second apertures. (In this case, flow-indication chamber 24 may be coupled to filter chamber 32 as in FIGS. 1-2, or filter chamber 32 may be omitted.)

In yet other such embodiments, tube constrictor 88 is configured to constrict exit tube 42. In other words, first appendage 90*a* and second appendage 90*b* protrude from filter chamber 32 in the downstream direction, i.e., the first and second appendages protrude beyond exit port 40, and exit tube 42 carries blood from exit port 40 through the first and second apertures. (In this case, flow-indication chamber 24 may be coupled to filter chamber 32 as in FIGS. 1-2, or flow-indication chamber 24 may be omitted.)

For those embodiments in which apparatus 20 comprises flow-indication chamber 24, the flow-indication chamber may contain any suitable moveable objects 46, such as wheel 54 or beads 48 (FIG. 1).

In some embodiments, the first and second appendages are continuous with the wall of the chamber from which the appendages protrude, i.e., the wall extends beyond the chamber so as to define the appendages. In other embodiments, the appendages are coupled to the wall of the chamber, e.g., using any suitable adhesive.

Typically, each appendage comprises a back arm 100, which protrudes from the chamber, and a front arm 102, which is angled (e.g., at approximately 90 degrees) with respect to back arm 100 and is shaped to define the aperture through which the tube passes.

Reference is now made specifically to inset portion 110 of FIG. 3, which shows the back of front arm 102 of first appendage 90a, i.e., the surface of the front arm that faces second appendage 90b.

In addition to first aperture 92a, first appendage 90a (e.g., front arm 102 of the first appendage) is shaped to define a first row 94a of one or more teeth 96. Similarly, as shown in FIGS. 4A-B, second appendage 90b (e.g., front arm 102 of the second appendage) is shaped to define a second row 94b of one or more teeth 96 parallel to first row 94a. As further described below with reference to FIGS. 4A-B, second row 94b is configured to interlock with first row 94a at multiple different relative positions of the first appendage and second appendage. In these different positions, second aperture 92b is aligned with first aperture 92a with different respective degrees of alignment such that coupling tube 84 (or any other tube passing through the apertures) is constricted with different respective degrees of constriction.

Figure 4A:
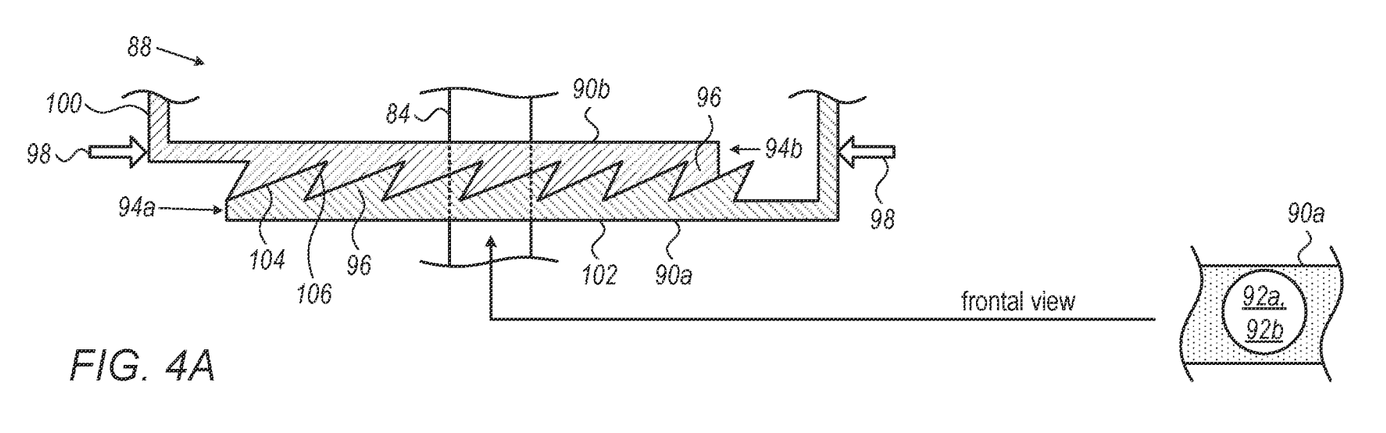
FIGS. 4A-B are schematic illustrations of a tube constrictor, in accordance with some embodiments of the present invention.
Figure 4B:
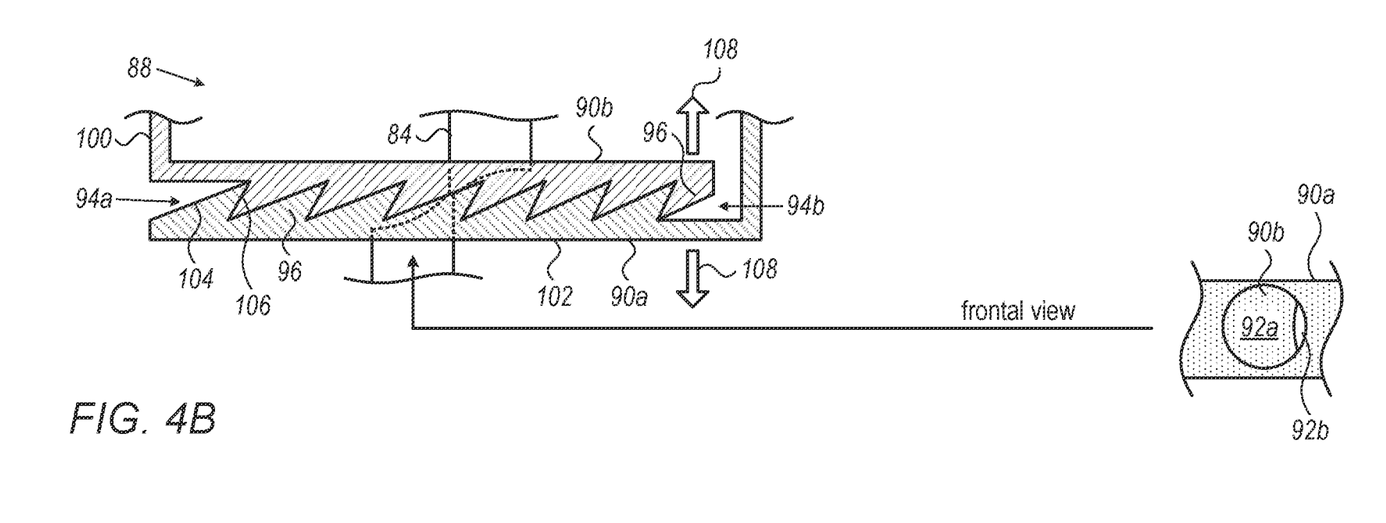

Reference is now made to FIGS. 4A-B, which are schematic illustrations of tube constrictor 88, in accordance with some embodiments of the present invention.

In FIG. 4A, the first and second appendages are at a first relative position in which second aperture 92b is aligned with first aperture 92a, such that coupling tube 84 is not constricted. Subsequently, one or both of the appendages may be shifted such that the appendages assume a second relative position in which the two apertures are less aligned with one another, and hence tube 84 is mostly constricted, as shown in FIG. 4B.

In some embodiments, as shown in FIGS. 4A-B, each tooth 96 is angled backward (e.g., toward back arm 100 of the appendage), such that the tooth comprises a longer front edge 104 and a shorter back edge 106. In such embodiments, the tube may be constricted by advancing the two rows of teeth relative to one another, e.g., by pushing at least one front arm 102 toward the back arm 100 of the other appendage. For example, as indicated in FIG. 4A by pinch indicators 98, the appendages may be pinched together, e.g., using a forefinger placed on one back arm 100 and a thumb placed on the other back arm. As one or both of the rows are advanced, front edges 104 slide across each other, until the rows of teeth interlock at the next position by virtue of the contact between back edges 106, which inhibits the rows from sliding backward.

In other embodiments, each tooth 96 is angled forward, toward the tip of the appendage. In such embodiments, the tube may be constricted by moving at least one row of teeth backward relative to the other row of teeth, e.g., by pulling at least one front arm 102 away from the back arm 100 of the other appendage.

In some embodiments, the first and second appendages are configured to revert to a default relative position, in which the tube is not constricted, upon a release of first row 94a and second row 94b from one another, as indicated in FIG. 4B by release indicators 108. In other words, at least one of the appendages is elastic, such that any movement from the default relative position causes the appendage to store elastic energy that, upon release of the rows from one another, causes the appendage to revert to the default position. Alternatively or additionally, upon release, the first and second appendages may revert to their default relative position due to elastic energy stored in the wall of the tube while the tube is constricted.

(It is emphasized that the appendages may be shaped to define fewer teeth than are shown in the figures. For example, one appendage may be shaped to define a single tooth, and the other appendage may be shaped to define N≥2 teeth, such that N degrees of constriction are provided.)

Typically, the tube is not completely constricted in any of the positions in which the rows of teeth interlock with one another. In other words, as shown in FIG. 4B, even at the most constricted interlocked position, the tube may remain partly (e.g., 10%-20%) unconstricted. Thus, advantageously, full constriction of the tube requires that the physician continuously apply a force to one or both of the appendages, such that the physician is unlikely to forget that the flow has been stopped. For example, in the scenario shown in FIG. 4B, full constriction of the tube may require a continuous pinching of the appendages. In the absence of a pinching force, the elastic energy stored in the appendages and/or the wall of the tube causes the appendages to revert to the most constricted interlocked position.

(For embodiments in which the teeth are angled backward, the most constricted interlocked position is that in which the frontmost tooth of one appendage locks against the backmost tooth of the other appendage. For embodiments in which the teeth are angled forward, the most constricted interlocked position is that in which the frontmost tooth of one appendage locks against the frontmost tooth of the other appendage.)

Alternatively to tube constrictor 88, apparatus 20 may comprise any other clamp that protrudes from one of the chambers and is configured to constrict a tube in fluid communication with the chamber. The clamp may be continuous with the wall of the chamber from which the clamp protrudes, or coupled to the wall of the chamber.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
   a chamber shaped to define a fluid port;
   a first appendage protruding from the chamber and shaped to define a first aperture and a first row of one or more teeth; and a second appendage protruding from the chamber and shaped to define a second aperture and a second row of one or more teeth parallel to the one or more teeth of the first row, the first aperture and the second aperture are each configured for receiving a tube extending therethrough, the tube in communication with the fluid port, the one or more teeth of the second row being configured to interlock with the one or more teeth of the first row at multiple different relative positions of the first appendage and second appendage in which the second aperture is aligned with the first aperture with different respective degrees of alignment such that the tube is constricted with different respective degrees of constriction, controlling a rate of blood flow through the tube.

2. The apparatus according to claim 1, wherein the chamber is configured to hold a blood filter therein.

3. The apparatus according to claim 1, further comprising one or more moveable objects disposed within the chamber and configured to move in response to a flowing of the blood through the chamber, at least a portion of a wall of the chamber being transparent so as to expose the one or more moveable objects to sight.

4. The apparatus according to claim 1, wherein the first appendage and second appendage are continuous with a wall of the chamber.

5. The apparatus according to claim 1, wherein the first appendage and second appendage are configured to revert to a default relative position, in which the tube is not constricted, upon a release of the first row and second row from one another.

6. The apparatus according to claim 1, wherein the first appendage comprises a first back arm, which protrudes from the chamber, and a first front arm, which is angled with respect to the first back arm and is shaped to define the first aperture and the one or more teeth of the first row, and wherein the second appendage comprises a second back arm, which protrudes from the chamber, and a second front arm, which is angled with respect to the second back arm and is shaped to define the second aperture and the one or more teeth of the second row.

7. The apparatus according to claim 1, wherein each of the one or more teeth in the first row and in the second row is angled backward, such that an advancement of the first row and second row relative to one another constricts the tube.

8. The apparatus according to claim 1, wherein the tube is not completely constricted in any of the positions.

9. A method, comprising:

sliding a first appendage, which protrudes from a chamber and is shaped to define a first aperture and a first row of one or more teeth, across a second appendage, which protrudes from the chamber and is shaped to define a second aperture and a second row of one or more teeth parallel to the first row of teeth, such that the one or more teeth of the second row interlocks with the one or more teeth of the first row at a relative position of the first appendage and second appendage in which the second aperture is misaligned with the first aperture, thereby constricting a tube extending through the first aperture and the second aperture and is in communication with a fluid port of the chamber to control a rate of blood flow through the tube; and subsequently to constricting the tube, releasing the one or more teeth of the first row and the one or more teeth of the second row from one another, thereby causing the first appendage and second appendage to revert to a default relative position in which the tube is not constricted.

10. The method according to claim 9, wherein the chamber holds a blood filter therein.

11. The method according to claim 9, wherein one or more moveable objects are disposed within the chamber and are configured to move in response to a flowing of the blood through the chamber, at least a portion of a wall of the chamber being transparent so as to expose the one or more moveable objects to sight.

12. The method according to claim 9, wherein the first appendage and second appendage are continuous with a wall of the chamber.

13. The method according to claim 9, wherein the first appendage includes a first back arm, which protrudes from the chamber, and a first front arm, which is angled with respect to the first back arm and is shaped to define the first aperture and the one or more teeth of the first row, and wherein the second appendage includes a second back arm, which protrudes from the chamber, and a second front arm, which is angled with respect to the second back arm and is shaped to define the second aperture and the one or more teeth of the second row.

14. The method according to claim 9, wherein each of the one or more teeth in the first row and in the second row is angled backward, and wherein sliding the first appendage across the second appendage comprises advancing the first row and second row relative to one another.

* * * * *